(12) United States Patent
Whitaker

(10) Patent No.: US 11,576,686 B2
(45) Date of Patent: Feb. 14, 2023

(54) BONE GRAFT HARVESTING

(71) Applicant: Innovasis, Inc., Salt Lake City, UT (US)

(72) Inventor: Camden Whitaker, Wichita, KS (US)

(73) Assignee: Innovasis, Inc., Salt Lake City, UT (US)

(*) Notice: Subject to any disclaimer, the term of this patent is extended or adjusted under 35 U.S.C. 154(b) by 252 days.

(21) Appl. No.: 16/916,867

(22) Filed: Jun. 30, 2020

(65) Prior Publication Data

US 2020/0405325 A1 Dec. 31, 2020

Related U.S. Application Data

(60) Provisional application No. 62/868,962, filed on Jun. 30, 2019.

(51) Int. Cl.
*A61B 17/16* (2006.01)

(52) U.S. Cl.
CPC .... *A61B 17/1635* (2013.01); *A61B 2217/005* (2013.01)

(58) Field of Classification Search
CPC .................. A61B 17/1635; A61B 17/1637
See application file for complete search history.

(56) References Cited

U.S. PATENT DOCUMENTS

2018/0049727 A1* 2/2018 Papenfuss ............ A61B 10/025

* cited by examiner

*Primary Examiner* — Andrew Yang
(74) *Attorney, Agent, or Firm* — Brooks, Cameron & Huebsch, PLLC

(57) ABSTRACT

The present disclosure includes apparatuses for a bone graft harvesting device. An example apparatus includes a blade tip including a proximal end and a distal end, wherein the distal end of the blade tip includes a number of blades configured to morcellate bone in response to being rotated and a lead tip located within the blade tip and configured to maintain the bone graft harvesting apparatus centered on a bone graft punch hole.

16 Claims, 3 Drawing Sheets

BONE GRAFT HARVESTING

PRIORITY INFORMATION

This application claims priority of U.S. Provisional Application Ser. No. 62/868,962, filed on Jun. 30, 2019, the content of which are incorporated herein by reference.

TECHNICAL FIELD

The present disclosure relates generally to bone graft harvesting, and more particularly, to removing and collecting bone graft material from a patient.

BACKGROUND

Bone graft material can be utilized in many surgical procedures and can be harvested from bone from the hip called the ilium, for example. Often, a simple chisel approach is employed to dig out bone which can result in a wound site that is more painful than the site in which the harvested bone is to be used.

Graft site morbidity refers to any consequences that result from the harvesting of a patient's own bone (e.g., an autograft). Undesirable side effects and complications that can result from the bone graft harvesting procedure include early post-operative pain, chronic pain, scarring, bleeding, infection, bone fracture, and more.

Autograft bone graft harvest is an important surgical technique for orthopedic surgeons. The iliac crest can provide a robust amount of bone graft, but using it carries a risk of complications. There are differences between the outcomes of anterior and posterior crest harvests. Anterior autograft harvest is associated with a higher complication rate. The posterior approach, however, is associated with more postoperative pain than the anterior approach, with the patient often experiencing more pain from the harvest than from the procedure itself. The all-cancellous iliac crest bone graft harvest provides the benefit of a large quantity of autogenous bone for various procedures, ranging from spinal fusion to osseous reconstruction.

In some procedures, rotational or reciprocating bone shavers are used to collect bone tissue. The surgeon will access the bone through the skin, muscle, and other tissue. Once accessed, the bone shaver is used to collect morcellated bone. If sufficient bone material is not obtained with one hole or punch, the surgeon may use the same site for more, going in a different direction or orientation each time. In some instances, these multiple holes can lead to complications such as delayed healing, pain, bone fracture, etc.

Various approaches have been used to harvest morcellated bone for use in spinal implants. Such approaches, however, have typically suffered from complications that arise at the site where the bone was removed.

DETAILED DESCRIPTION

Figure 1A:
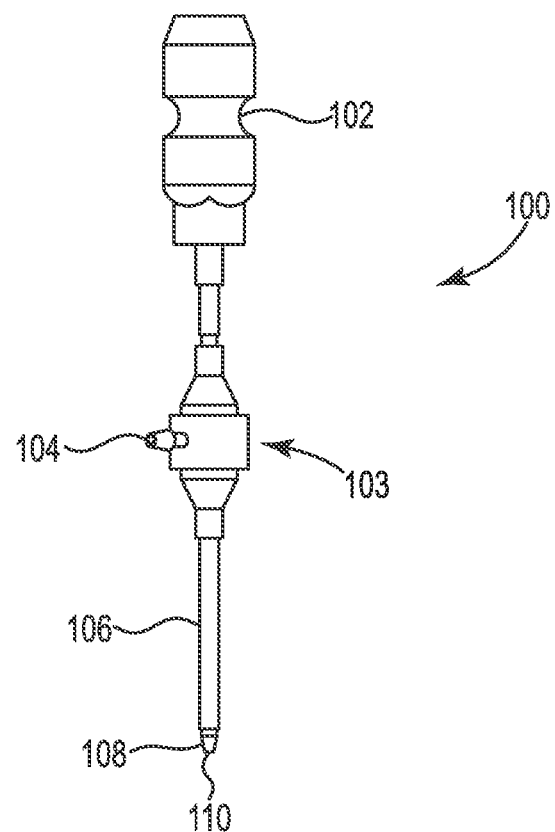
FIG. 1A is a schematic diagram of a bone graft harvesting apparatus in accordance with a number of embodiments of the present disclosure.

The present disclosure includes apparatuses and methods for bone graft harvesting. An example apparatus includes a blade tip including a proximal end and a distal end, wherein the distal end of the blade tip includes a number of blades configured to morcellate bone in response to being rotated and a lead tip located within the blade tip and configured to maintain the bone graft harvesting apparatus centered on a bone graft punch hole.

Bone grafting is a surgical procedure that replaces missing bone with material from patient's own body, an artificial, synthetic, or natural substitute. Bone grafting is possible because bone tissue has the ability to regenerate completely if provided the space into which it has to grow. As natural bone grows, it generally replaces the graft material completely, resulting in a fully integrated region of new bone. Bone graft material can be classified into three groups: autograft bone grafts, which are a graft of tissue from one point to another of the same individual's body; allograft bone graft, which involves tissue graft from a donor of the same species as the recipient but not genetically identical; and synthetic bone grafts, which can be ceramics or injectable cement based and may include morphogenic proteins, growth factors, cells, or combinations thereof.

An autograft bone graft is harvested from a patient's bone via the use of a bone drill, scraper, punch, or the like. Usually, the graft is taken from the iliac crest or ilium, but can be taken from the proximal femur or distal femur or other bones. In one method, the bone is harvested by use of a hollow tube which has teeth or knife-like features on the distal end. The surgeon will rotate the device to harvest the bone. During the rotation, the sharp distal end will morcellate (e.g., granulate) the bone tissue. The harvest location will be a cylindrical punch or hole in the target bone, generally 3 to 8 mm in diameter and 50 to 75 mm in length. If more bone graft material is needed, the surgeon will drill another cylindrical punch, in some instances using the top of the existing punch hole and orientating the device in a different direction. When sufficient bone graft material has been obtained, the surgeon will then use the bone tissue in, for example, a spinal fusion procedure.

Occasionally problems such as post-op pain, nerve injury, bone fracture, or infection may result. In some examples, complications can be reduced if the procedure requires only a single punch. The disclosed bone graft harvesting apparatus accomplishes this by, for example, using an existing 3 to 8 millimeter (mm) diameter punch hole and expanding the diameter of the punch hole to 8 to 12 mm.

The bone graft punch hole can be an existing punch hole shaped like a cylindrical column with a depth of 50 to 75 mm, for example. If additional bone graft material is needed the bone graft harvesting apparatus can be used to collect the additional bone graft material using the existing punch hole. For example, a physician can access an iliac, iliac crest, ilium, femur, rib, rib cage, or other bone by opening a patient's skin, moving aside muscle and other tissue, create a bone graft harvesting punch hole using a different device, and use the bone graft harvesting apparatus to collect additional bone from the existing bone graft punch hole if additional bone graft material is needed. The bone graft material can be collected from all four layers of bone including the periosteum, the cortical (e.g., hard bone), the cancellous (e.g., spongy bone), and/or the bone marrow. If the physician obtained preferred bone graft material, for example cortical, cancellous, and/or a mixture, in the bone graft punch hole, the physician can use the bone graft harvesting apparatus in the same bone graft punch hole to produce similar bone graft material.

Each blade of the number of blades of the bone graft harvesting apparatus can include a tip and a curved surface. The tip can be a sharp surface to morcellate bone of a patient when the blade is in contact with the bone and the blade tip is rotating. The curved surface is shaped to move morcellated bone graft material away from the morcellated bone when the blade tip is rotating.

The lead tip can include a number of windows (e.g., openings) to receive the morcellated bone graft material. For example, a curved surface of a blade can move morcellated bone graft material to a window of the lead tip.

The lead tip can include a nose that extends distally past the number of blades of the blade tip. The nose of the lead tip can be placed into an existing bone graft punch hole. The bone graft harvesting apparatus can be maintained and/or centered in the existing bone graft punch hole by the lead tip. The lead tip can be tapered to maintain a centered position in a number of different size punch holes. The tapered lead tip can even maintain the bone graft harvesting apparatus centered as the bone graft punch hole increases.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", etc., particularly with respect to reference numerals in the drawings, indicate that a number of the particular feature so designated can be included. It is also to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the handle, as appropriate to the context.

The figures herein follow a numbering convention in which the first digit or digits correspond to the figure number and the remaining digits identify an element or component in the figure. Similar elements or components between different figures may be identified by the use of similar digits. For example, 108 may reference element "8" in FIG. 1A, and a similar element may be referenced as 208 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1A is a schematic diagram of a bone graft harvesting apparatus 100 in accordance with a number of embodiments of the present disclosure. The bone graft harvesting apparatus 100 can include a handle 102, a mid-section 103, a shaft 106, a blade tip 108, and a lead tip 110.

The bone graft harvesting apparatus 100 can include the handle 102 on its proximal end. The handle 102 can be rotated by a user (e.g., a physician). In some examples, the blade tip 108 will rotate in response to the handle 102 being rotated. The handle 102 can be coupled to the mid-section 103.

The mid-section 103 can be positioned between and coupled to the handle 102 and the shaft 106. In a number of embodiments, the mid-section 103 can include a vacuum port 104, an outer cylinder (e.g., outer cylinder 112 in FIG. 1B), and an inner cylinder (e.g., inner cylinder 114 in FIG. 1B). The vacuum port 104 can be positioned between and coupled to the outer cylinder and a vacuum, a syringe, or a suction system to provide vacuum (e.g., suction). In some examples, the vacuum port 104 position and/or vacuum can be maintained even when the handle 102 is rotated because the outer cylinder does not need to be rotated with respect to the inner cylinder. For example, the outer cylinder is rotatable relative to the inner cylinder and/or the inner cylinder is rotatable relative to the outer cylinder. The vacuum can be applied to the interior cylinder and the central lumen (e.g., central lumen 111 in FIG. 1B) of the shaft 106 to aspirate the bone graft material, that is generated by rotation of blade tip 108, into the interior cylinder and/or the central lumen of the shaft 106.

The shaft 106 can be positioned between the mid-section 103 and the blade tip 108. In some examples, the shaft 106 is non-rotationally coupled to the mid-section 103 and/or the inner cylinder and as a result the shaft 106 may not rotate when the handle 102 is rotated. In a number of embodiments, the proximal end of the shaft 106 can be directly or indirectly coupled to the handle 102.

The bone graft material can be received and/or collected in the central lumen of shaft 106 and/or moved through the central lumen of shaft 106 to the inner cylinder. The shaft 106 can be detachable (e.g., decoupled) from the bone graft harvesting apparatus 100. In some examples, the bone graft material can be recovered by removing the shaft 106 from the inner cylinder.

A proximal end of the blade tip 108 can be coupled to the distal end of the shaft 106. A cylindrical body (e.g., cylindrical body 222 in FIG. 2) and a number of blades (e.g., blades 220-1, 220-2, . . . , 220-X in FIG. 2) can be included in the blade tip 108. The number of blades can be located on the distal end of the blade tip 108. The blade tip 108 can include four blades, for example. In some examples, the blades can be as thick as the walls of the cylindrical body of the blade tip 108. The blade tip 108 and/or the number of blades can contact and morcellate bone in response to the blade tip 108 being rotated. For example, a tip (e.g., tip 328 in FIG. 3) can dig into the bone to morcellate the bone when the blade tip 108 is rotated.

Blade tip 108 can be rotated and advanced down an existing punch hole so that additional bone graft material from for example, the sides of an existing punch hole, can be collected in response to rotation of the handle 102. In some examples, a drive shaft, not shown, can be coupled to handle 102 at the drive shaft's proximal end and to the distal end of the blade tip 108, as a result, rotation of handle 102 will rotate blade tip 108 without rotating the inner cylinders, the outer cylinders, and/or the shaft 106.

Morcellated bone graft material can be moved by the blade tip 108. For example, the blade tip 108 can include a curved surface (e.g., curved surface 336 in FIG. 3) that moves the morcellated bone graft material away from the morcellated bone and towards a window (e.g., windows 424-1 and 424-2 in FIG. 4) when the blade tip 108 is rotated.

The lead tip 110 can be positioned within blade tip 108. The lead tip 110 can include a nose (e.g., nose 426 in FIG. 4), a number of windows (e.g., windows 424-1 and 424-2 in FIG. 4), a central lumen (e.g., central lumen 437 in FIG. 4), and a proximal body (e.g., proximal body 438 in FIG. 4). The proximal body of lead tip 110 fits into and is retained within blade tip 108.

An existing bone graft punch hole in a bone can be accessed and the nose of the lead tip 110 can be placed into the existing bone graft punch hole. The nose of lead tip 110 can extend distally past blade tip 108 and can ensure the blade tip 108 stays centered around the existing punch hole as the blade tip 108 is rotated and advanced down the existing punch hole. The lead tip can be tapered to maintain the blade tip 108 in a centered position in a number of different size punch holes and can maintain the blade tip 108 centered as the diameter of the existing punch hole increases.

Figure 1B:
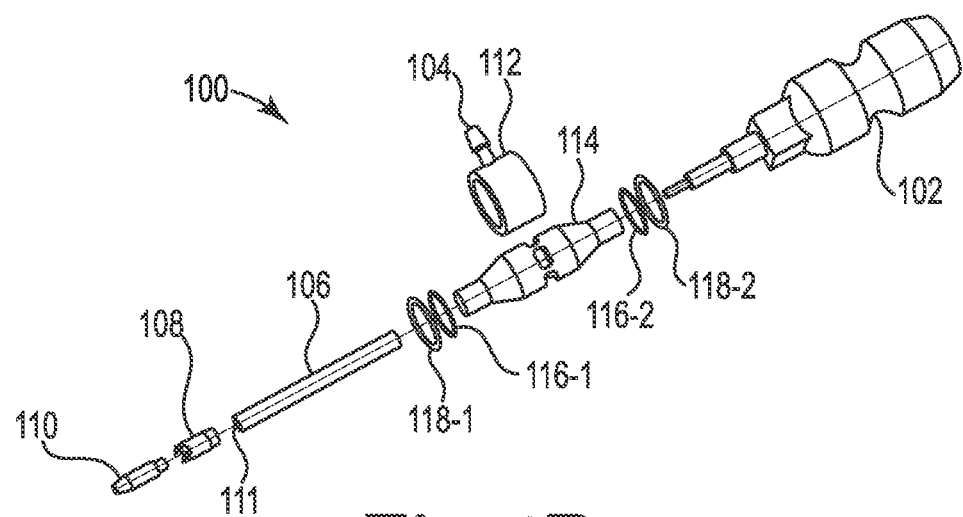
FIG. 1B is an exploded view of a bone graft harvesting apparatus in accordance with a number of embodiments of the present disclosure.

FIG. 1B is an exploded view of a bone graft harvesting apparatus 100 in accordance with a number of embodiments of the present disclosure. The bone graft harvesting apparatus 100 can include a handle 102, a vacuum port 104, a shaft 106 with a central lumen 111, a blade tip 108, and a lead tip 110. As illustrated in FIG. 1B, the bone graft harvesting apparatus 100 can further include an outer cylinder 112, an inner cylinder 114, O-rings 116-1 and 116-2, and retaining rings 118-1 and 118-2.

The outer cylinder 112 can be included in the mid-section (e.g., mid-section 103 in FIG. 1B) of the bone graft harvesting apparatus 100. The outer cylinder 112 can be non-rotationally attached to the handle 102. For example, the outer cylinder 112 does not rotate in response to the handle 102 rotating.

The outer cylinder 112 can include a vacuum port 104. The vacuum port 104 can be positioned between and coupled to a vacuum, a syringe, or a suction system and the outer cylinder 112. In some examples, the position of the vacuum port 104 and/or vacuum can be maintained even when the handle 102 is rotated because the outer cylinder 112 is rotatable relative to the inner cylinder 114 and/or the inner cylinder 114 is rotatable relative to the outer cylinder 112. The vacuum can be applied to the interior cylinder and a central lumen 111 of the shaft 106 to aspirate the bone graft material that is generated by rotation of blade tip 108 into the central lumen 111 of the shaft 106 and/or the inner cylinder 114.

In a number of embodiments, gaskets, for example, O-rings 116-1 and 116-2 located in O-ring grooves (e.g., O-ring grooves 740-1 and 740-2 in FIG. 7) on the exterior of inner cylinder 114 and retaining rings 118-1 and 118-2 located in retaining ring grooves (e.g., retaining ring grooves 742-1 and 742-2 in FIG. 7) on the exterior of inner cylinder 114, can be positioned between the inner cylinder 114 and the outer cylinder 112 to provide a vacuum seal to an interface of the outer cylinder 112 and the inner cylinder 114.

The inner cylinder 114 can be included in the mid-section of the bone graft harvesting apparatus 100 and can be positioned inside of outer cylinder 112. In some examples, the inner cylinder 114 can be positioned between and/or coupled to the handle 102 and the shaft 106. The bone graft material can be moved through the central lumen 111 of the shaft 106 to the inner cylinder 114. In a number of embodiments, the bone graft material can be moved using a vacuum. The inner cylinder 114 can include openings (e.g., openings 744-1, 744-2, . . . , 744-Y in FIG. 7) to allow the vacuum to be applied to the interior of inner cylinder 114 and the central lumen 111 of the shaft 106.

The inner cylinder can store (e.g., collect) the bone graft material. The bone graft material can be recovered by removing the shaft 106 from the inner cylinder 214. In some examples, the inner cylinder 214 can include an opening, not shown, to retrieve the bone graft material.

Figure 2:
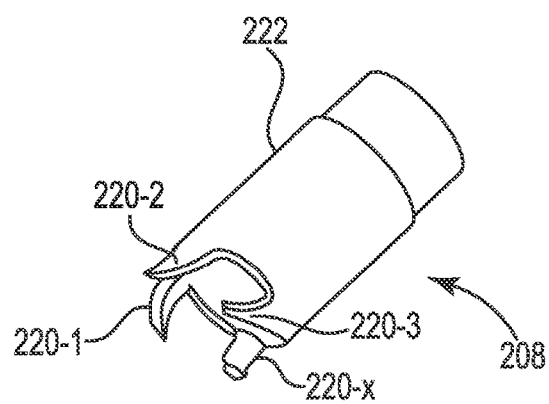
FIG. 2 is a schematic diagram of a blade tip of a bone graft harvesting apparatus in accordance with a number of embodiments of the present disclosure.

FIG. 2 is a schematic diagram of a blade tip 208 of a bone graft harvesting apparatus (e.g., bone graft harvesting apparatus 100 in FIGS. 1A and 1B) in accordance with a number of embodiments of the present disclosure. A proximal end of the blade tip 208 can be coupled to a distal end of a shaft (e.g., shaft 106 in FIGS. 1A and 1B).

The blade tip 208 can include a number of blades 220-1, 220-2, 220-3, . . . , 220-X and a cylindrical body 222. The number of blades 220-1, . . . , 220-X can be located on the distal end of the blade tip 208. As illustrated in FIG. 2, the blade tip 208 can include four blades 220-1, . . . , 220-X. In some examples, the blades 220-1, . . . , 220-X can be as thick as the walls of the cylindrical body 222 of the blade tip 208. The blades 220-1, . . . , 220-X can be flat or serrated. The blade tip 208 and/or the number of blades 220-1, . . . , 220-X can contact and morcellate bone in response to the blade tip 108 being rotated. For example, a tip (e.g., tip 328 in FIG. 3) can dig into the bone to morcellate the bone when the blade tip 208 is rotated.

Blade tip 208 can be rotated and advanced down an existing punch hole so that additional bone graft material can be collected in response to rotation of a handle (e.g., handle 102 in FIGS. 1A and 1B). In some examples, a drive shaft, not shown, can be coupled to the handle at the drive shaft's proximal end and to the distal end of the blade tip 208, as a result, rotation of the handle will rotate blade tip 208.

Morcellated bone graft material can be moved by the blade tip 208. For example, the blade tip 208 can include a curved surface (e.g., curved surface 336 in FIG. 3) that moves the morcellated bone graft material away from the morcellated bone and towards a window (e.g., windows 424-1 and 424-2 in FIG. 4) when the blade tip 208 is rotated.

Figure 3:
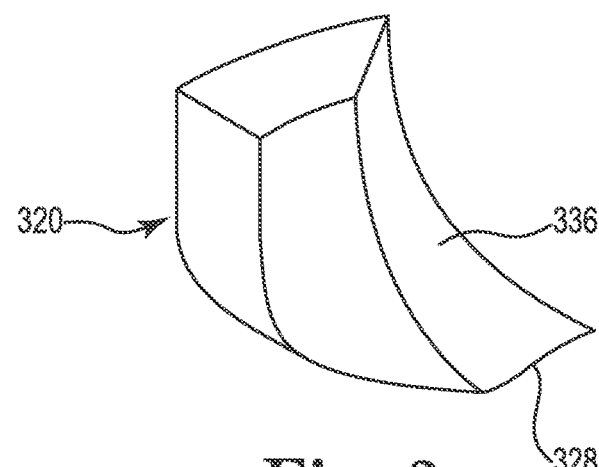
FIG. 3 is a schematic diagram of a blade of a blade tip in accordance with a number of embodiments of the present disclosure.

FIG. 3 is a schematic diagram of a blade 320 of a blade tip (e.g., blade tip 108 and 208 in FIGS. 1A, 1B, and 2, respectively) in accordance with a number of embodiments of the present disclosure. The blade 320 can include a tip 328 and a curved surface 336. The tip 328 can dig into a bone to morcellate the bone while the curved surface 336 moves the morcellated bone graft material away from the morcellated bone and towards a window (e.g., windows 424-1 and 424-2 in FIG. 4) when the blade tip is rotated. In some examples, the curved surface 336 can move the morcellated bone graft material towards the center of the bone graft harvesting apparatus (e.g., bone graft harvesting apparatus 100 in FIGS. 1A and 1B).

Figure 4:
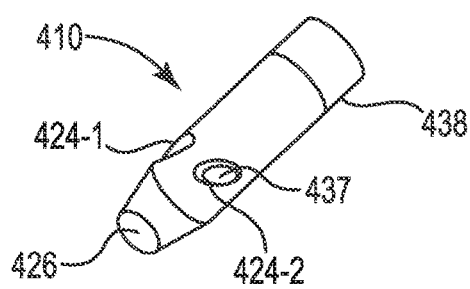
FIG. 4 is a schematic diagram of a lead tip of a bone graft harvesting apparatus in accordance with a number of embodiments of the present disclosure.

FIG. 4 is a schematic diagram of a lead tip 410 of a bone graft harvesting apparatus (e.g., bone graft harvesting apparatus 100 in FIGS. 1A and 1B) in accordance with a number of embodiments of the present disclosure. The lead tip 410 can be positioned within a blade tip (e.g., blade tip 108 and 208 in FIGS. 1A, 1B, and 2, respectively). The lead tip 410 can include a nose 426, a number of windows 424-1 and 424-2, a central lumen 437, and a proximal body 438. The proximal body 438 of lead tip 410 fits into and is retained within a blade tip.

The nose 426 of the lead tip 410 can be placed into an existing bone graft punch hole. The nose 426 of lead tip 410 can extend distally past a blade tip and can ensure the blade tip stays centered around the existing punch hole as the blade tip is rotated and advanced down the existing punch hole. The lead tip 410 can be tapered to maintain the blade tip in a centered position in a number of different size punch holes and maintain the blade tip centered as the bone graft punch hole diameter is increased.

Figure 5:
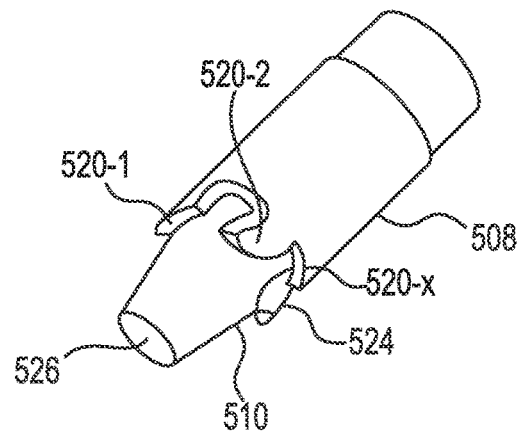
FIG. 5 is a schematic diagram of a lead tip within a blade tip in accordance with a number of embodiments of the present disclosure.

FIG. 5 is a schematic diagram of a lead tip 510 within a blade tip 508 in accordance with a number of embodiments of the present disclosure. The lead tip 510 can include a nose 526 and a window 524 and the blade tip 508 can include a number of blades 520-1, 520-2, . . . , 520-X. The lead tip 510 fits into and is retained within the blade tip 508. The number of blades 520-1, 520-2, . . . , 520-X of the blade tip 508 can dig into a bone to morcellate the bone while the curved surface (e.g., curved surface 336 in FIG. 3) of the blades 520-1, . . . , 520-X move the morcellated bone graft material away from the morcellated bone and towards the window 524 when the blade tip 508 is rotated.

Figure 6:
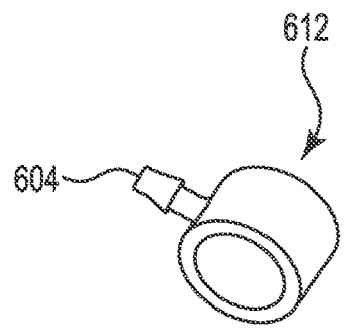
FIG. 6 is a schematic diagram of an outer cylinder of a mid-section of a bone graft harvesting apparatus in accordance with a number of embodiments of the present disclosure.

FIG. 6 is a schematic diagram of an outer cylinder 612 of a mid-section (e.g., mid-section 103 in FIG. 1A) of a bone graft harvesting apparatus (e.g., bone graft harvesting apparatus 100 in FIGS. 1A and 1B) in accordance with a number of embodiments of the present disclosure. The outer cylinder 612 can be non-rotationally attached to a handle (e.g., handle 102 in FIGS. 1A and 1B). For example, the outer cylinder 612 may not rotate in response to the handle rotating.

The outer cylinder 612 can include a vacuum port 604. The vacuum port 604 can be positioned between and coupled to a vacuum, a syringe, or a suction system and the outer cylinder 612. In some examples, the position of the vacuum port 604 and/or the vacuum can be maintained even when the handle is rotated because the outer cylinder 612 is rotatable relative to the inner cylinder (e.g., inner cylinder 114 in FIGS. 1A and 1B) and/or the inner cylinder is rotatable relative to the outer cylinder 612. The vacuum can be applied to the interior of the inner cylinder and a central lumen (e.g., central lumen in FIG. 1B) of a shaft (e.g., shaft 106 in FIGS. 1A and 1B) to aspirate the bone graft material that is generated by rotation of a blade tip (e.g., blade tip 108, 208, and 508 in FIGS. 1A, 1B, 2, and 5, respectively) into the central lumen of the shaft and/or the interior of the inner cylinder.

Figure 7:
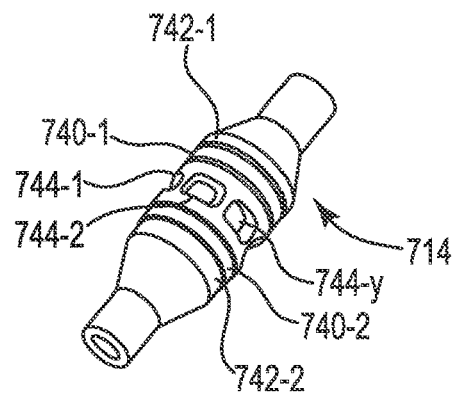
FIG. 7 is a schematic diagram of an inner cylinder of a mid-section of a bone graft harvesting apparatus in accordance with a number of embodiments of the present disclosure.

FIG. 7 is a schematic diagram of an inner cylinder 714 of a mid-section (e.g., mid-section 103 in FIG. 1A) of a bone graft harvesting apparatus (e.g., bone graft harvesting apparatus 100 in FIGS. 1A and 1B) in accordance with a number of embodiments of the present disclosure.

The inner cylinder 714 can be positioned inside of an outer cylinder (e.g., outer cylinder 112 and 612 in FIGS. 1A, 1B, and 6, respectively). In some examples, the inner cylinder 714 can be positioned between and/or coupled to a handle (e.g., handle 102 in FIGS. 1A and 1B) and the shaft (e.g., shaft 106 in FIGS. 1A and 1B). The bone graft material can be moved through a central lumen (e.g., central lumen 111 in FIG. 1B) of the shaft to an interior of the inner cylinder 714. In a number of embodiments, the bone graft material can be moved using a vacuum. The inner cylinder 714 can include openings 744-1, 744-2, . . . , 744-Y to allow the vacuum to be applied to the interior of the inner cylinder 714 and the central lumen of the shaft.

In a number of embodiments, gaskets, for example, O-rings (e.g., O-rings 116-1 and 116-2 in FIG. 1B) can be located in O-ring grooves 740-1 and 740-2 on the exterior of the inner cylinder 714 and retaining rings (e.g., retaining rings 118-1 and 118-2 in FIG. 1B) can be located in retaining ring grooves 742-1 and 742-2 on the exterior of the inner cylinder 714, can be used to provide a vacuum seal to an interface of the outer cylinder and the inner cylinder 714.

The inner cylinder 714 can store the bone graft material. The bone graft material can be recovered by removing the shaft from the inner cylinder 714. In some examples, the inner cylinder 714 can include an opening, not shown, to retrieve the bone graft material.

Figure 8:
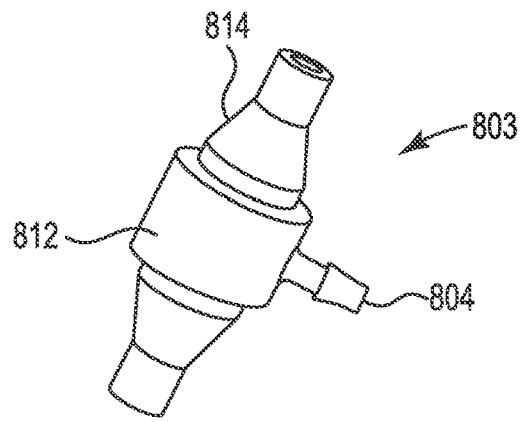
FIG. 8 is a schematic diagram of a mid-section of a bone graft harvesting apparatus in accordance with a number of embodiments of the present disclosure.

FIG. 8 is a schematic diagram of a mid-section 803 of a bone graft harvesting apparatus (e.g., bone graft harvesting apparatus 100 in FIGS. 1A and 1B) in accordance with a number of embodiments of the present disclosure. The mid-section 803 can include an outer cylinder 812 and an inner cylinder 814.

The outer cylinder 812 can be non-rotationally attached to a handle (e.g., handle 102 in FIGS. 1A and 1B) so that the outer cylinder 812 may not rotate in response to the handle rotating. The outer cylinder 812 can include a vacuum port 804. The vacuum port 804 can be positioned between and coupled to a vacuum, a syringe, or a suction system and the outer cylinder 812. In some examples, the position of the vacuum port 804 and vacuum can be maintained even when the handle is rotated because the outer cylinder 812 is rotatable relative to the inner cylinder 814 and/or the inner cylinder 814 is rotatable relative to the outer cylinder 812. The vacuum can be applied to the interior of the inner cylinder 814 and a central lumen (e.g., central lumen 111 in FIG. 1B) of a shaft (e.g., shaft 106 in FIGS. 1A and 1B) to aspirate the bone graft material that is generated by rotation of a blade tip (e.g., blade tip 108, 208, and 508 in FIGS. 1A, 1B, 2, and 5, respectively) into the central lumen of the shaft and/or the interior of the inner cylinder 814.

In a number of embodiments, gaskets, for example, O-rings (e.g., O-rings 116-1 and 116-2 in FIG. 1B) located in O-ring grooves (e.g., O-ring grooves 740-1 and 740-2 in FIG. 7) on the exterior of inner cylinder 814 and/or retaining rings (e.g., retaining rings 118-1 and 118-2 in FIG. 1B) located in retaining ring grooves (e.g., retaining ring grooves 742-1 and 742-2 in FIG. 7) on the exterior of inner cylinder 814, can be used to provide a vacuum seal to an interface of the outer cylinder 812 and the inner cylinder 814.

The inner cylinder 814 can be included in the mid-section 803 of the bone graft harvesting apparatus and can be positioned inside of outer cylinder 812. In some examples, the inner cylinder 814 can be positioned between and/or coupled to the handle and the shaft. The bone graft material can be moved through the central lumen (e.g., central lumen 111 in FIG. 1B) of the shaft to the inner cylinder 814. In a number of embodiments, the bone graft material can be moved using a vacuum. The inner cylinder 814 can include openings (e.g., openings 744-1, 744-2, . . . , 744-Y in FIG. 7) to allow the vacuum to be applied to the interior of inner cylinder 814 and the central lumen of the shaft.

The inner cylinder 814 can store the bone graft material. The bone graft material can be recovered by removing the shaft from the inner cylinder 814. In some examples, the inner cylinder 814 can include an opening, not shown, to retrieve the bone graft material.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A bone graft harvesting apparatus, comprising:
   a blade tip including a proximal end and a distal end, wherein the distal end of the blade tip includes a number of blades configured to morcellate bone in response to being rotated, wherein each blade of the number of blades include a tip and a curved surface, and wherein the curved surface of each blade is configured to move morcellated bone graft material away from the morcellated bone; and
   a lead tip located within the blade tip and configured to maintain the bone graft harvesting apparatus centered on a bone graft punch hole, wherein the lead tip includes a number of windows configured to receive the morcellated bone graft material.

2. The apparatus of claim 1, wherein the number of blades on the blade tip comprise four blades.

3. The apparatus of claim 1, wherein the lead tip includes a nose that extends distally past the number of blades.

4. The apparatus of claim 3, wherein the nose of the lead tip is tapered.

5. A bone graft harvesting apparatus, comprising:
   a handle;
   a shaft including a proximal end, a distal end, and a central lumen;
   a mid-section positioned between the handle and the shaft, wherein the mid-section comprises an inner cylinder and an outer cylinder, wherein the outer cylinder is rotatable relative to the inner cylinder, and wherein a distal end of the mid-section is coupled to the proximal end of the shaft; and
   a blade tip including a proximal end and a distal end, wherein the proximal end of the blade tip is coupled to the distal end of the shaft, and wherein the distal end of the blade tip includes a number of blades.

6. The apparatus of claim 5, wherein a central lumen of the shaft is configured to receive bone graft material.

7. The apparatus of claim 5, wherein the shaft is detachable from the bone graft harvesting apparatus.

8. The apparatus of claim 5, wherein a vacuum port is coupled to the outer cylinder.

9. The apparatus of claim 8, further comprising a number of gaskets positioned between the inner cylinder and the outer cylinder to provide a seal for the vacuum.

10. A method for obtaining a bone graft, comprising
    accessing an existing bone graft punch hole in a bone;
    placing a lead tip of a bone graft harvester into the existing bone graft punch hole;
    rotating a handle of the bone graft harvester;
    rotating a blade tip in contact with the bone and morcellating the bone in response to rotating the handle; and
    collecting morcellated bone graft material from the bone in response to rotating the blade.

11. The method of claim 10, wherein collecting morcellated bone graft material includes the blade tip moving the morcellated bone graft material away from the morcellated bone in response to rotating the blade tip.

12. The method of claim 10, wherein collecting morcellated bone graft material includes receiving the morcellated bone graft material within a central lumen of a shaft via a number of windows of the lead tip in response to rotating the blade tip.

13. The method of claim 10, wherein collecting morcellated bone graft material includes providing vacuum via a vacuum port to aspirate the morcellated bone graft material.

14. The method of claim 10, wherein collecting morcellated bone graft material includes storing the morcellated bone graft material within an inner cylinder coupled to the shaft.

15. The method of claim 14, further comprising recovering the morcellated bone graft material from the inner cylinder.

16. The method of claim 15, wherein recovering the morcellated bone graft material from the inner cylinder includes removing the shaft from the inner cylinder.

* * * * *